US008592632B2

(12) United States Patent
Dahmen et al.

(10) Patent No.: US 8,592,632 B2
(45) Date of Patent: Nov. 26, 2013

(54) PROCESS FOR PREPARING CYCLIC DIAMINES

(75) Inventors: Kirsten Dahmen, Freinsheim (DE); Martin Ernst, Heidelberg (DE); Michael Limbach, Worms (DE); Johann-Peter Melder, Böhl-Iggelheim (DE); Beatrice Rössler-Feigel, Weisenheim am Sand (DE); Joaquim Henrique Teles, Otterstadt (DE)

(73) Assignee: BASF SE, Ludwigshafen (DE)

( * ) Notice: Subject to any disclaimer, the term of this patent is extended or adjusted under 35 U.S.C. 154(b) by 239 days.

(21) Appl. No.: 13/128,508

(22) PCT Filed: Nov. 6, 2009

(86) PCT No.: PCT/EP2009/064751
§ 371 (c)(1),
(2), (4) Date: May 10, 2011

(87) PCT Pub. No.: WO2010/054988
PCT Pub. Date: May 20, 2010

(65) Prior Publication Data
US 2011/0218323 A1    Sep. 8, 2011

(30) Foreign Application Priority Data

Nov. 11, 2008  (EP) ..................................... 08168819

(51) Int. Cl.
*C07C 209/26*  (2006.01)

(52) U.S. Cl.
USPC .......................................... 564/446; 564/445

(58) Field of Classification Search
USPC ................................. 564/445, 446
See application file for complete search history.

(56) References Cited

U.S. PATENT DOCUMENTS

| | | | |
|---|---|---|---|
| 2,217,632 A | 10/1940 | Wolfe | |
| 2,262,002 A | 11/1941 | Hopff et al. | |
| 3,656,899 A | 4/1972 | Baechle et al. | |
| 4,429,157 A | 1/1984 | Disteldorf et al. | |
| 5,126,426 A | 6/1992 | Haseyama et al. | |
| 5,371,292 A | 12/1994 | Merger et al. | |
| 5,504,254 A | 4/1996 | Haas et al. | |
| 5,849,257 A | 12/1998 | Fujiwara et al. | |
| 5,852,217 A | 12/1998 | Haas et al. | |
| 6,100,430 A | 8/2000 | Yamamoto et al. | |

FOREIGN PATENT DOCUMENTS

| | | |
|---|---|---|
| CA | 2093374 A1 | 10/1993 |
| CN | 1046522 A | 10/1990 |
| DE | 710131 C | 9/1941 |
| DE | 3137898 A1 | 4/1983 |
| DE | 4210311 A1 | 10/1993 |
| EP | 0042119 A2 | 12/1981 |
| EP | 0394058 A1 | 10/1990 |
| EP | 0449089 A1 | 10/1991 |
| EP | 0564818 A2 | 10/1993 |
| EP | 0659734 A1 | 6/1995 |
| EP | 0816323 A2 | 1/1998 |
| FR | 1537011 A | 8/1968 |
| GB | 649680 A | 1/1951 |
| GB | 1515473 A | 6/1978 |
| TW | 491870 B | 6/2002 |
| WO | WO-98/25698 A1 | 6/1998 |

OTHER PUBLICATIONS

M. Winkler et al., Nitrilases Catalyze Key Step to Conformationally Constrained GABA Analogous gamma-Amino Acids in High Optical Purity, Journal of Organic Chemistry, No. 72, Aug. 23, 2007, pp. 7423-7426.

*Primary Examiner* — Brian J Davis
(74) *Attorney, Agent, or Firm* — Novak Druce Connolly Bove + Quigg LLP

(57) ABSTRACT

The present invention relates to a process for preparing a cyclic diamine, comprising the reaction of at least one cyclic alkene with a gas mixture (G) comprising dinitrogen the subsequent conversion of monoxide to give at least one cyclic ketone and then converting the at least one cyclic ketone to a cyclic diamine. The invention also relates to the use of a cyclic diamine with primary and secondary amine functions thus obtained to prepare polyamides and polyurethanes.

17 Claims, No Drawings

PROCESS FOR PREPARING CYCLIC DIAMINES

CROSS-REFERENCE TO RELATED APPLICATIONS

This application is a national stage application (under 35 U.S.C. §371) of PCT/EP2009/064751, filed Nov. 6, 2009, which claims benefit of European application 08168819.4, filed Nov. 11, 2008.

BACKGROUND OF THE INVENTION

The present invention relates to a process for preparing at least one cyclic diamine, comprising the reaction of at least one cyclic alkene with a gas mixture (G) comprising dinitrogen monoxide to give at least one cyclic ketone and the subsequent conversion of the at least one cyclic ketone to a cyclic diamine. The invention additionally relates to the use of the cyclic diamines with primary and/or secondary amine functions thus obtained to prepare polyamides and polyurethanes.

Processes for preparing cyclic diamines are known in principle from the prior art. For example, FR 1 537 011 discloses a process for preparing cyclic diamines by catalytically hydrogenating aminonitriles which are obtained from bicyclic lactams. The use of the amines to prepare polyamides and polyurethanes is likewise described.

DE 42 10 311 relates to a process for preparing cyclic diamines from symmetric aldazines and ketazines by hydrogenating azine cleavage by means of hydrogen, the hydrogenation being effected in the presence of ammonia and specific catalysts, for example Raney nickel or cobalt catalysts. DE 42 10 311 describes, for example, the preparations performed in this way of isophoronediamine and 3-methylaminocyclohexylamine.

EP 0 394 058 A1 also describes a process for preparing cyclic diamines for preparing polyamides and epoxy resins. This affords the diamines by catalytic hydrogenation of aromatic diamines.

It is known that cyclic diamines, including in particular commercial isophoronediamine (IPDA), can be used in the preparation of polyaddition resins from the group of the epoxy resins, polyurethane resins and polyurea resins. Reference is made by way of example to DE-A 31 37 898, GB patent 1 515 473 and EP 0 564 818.

The synthesis methods described in the prior art for preparing such cyclic diamines are inconvenient and costly.

SUMMARY OF THE INVENTION

Proceeding from this prior art, it was an object of the present invention to provide an alternative preparation process for cyclic diamines, which is simple and inexpensive.

This object is achieved in accordance with the invention by a process for preparing at least one cyclic diamine selected from diamines of the formulae (Ia), (Ib), (Ic) and (Id)

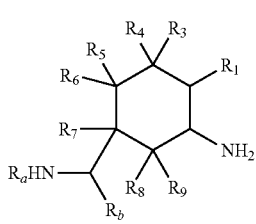

(Ia)

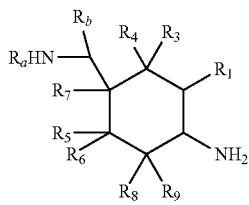

(Ib)

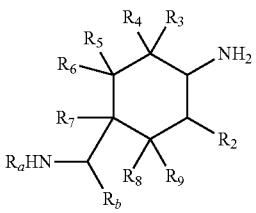

(Ic)

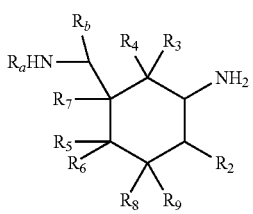

(Id)

where the $R_1$, $R_2$, $R_3$, $R_4$, $R_5$, $R_6$, $R_7$, $R_8$, $R_9$, $R_a$, $R_b$ radicals are each independently selected from the group consisting of H and alkyl;

and where $R_1$ or $R_2$ is, or $R_1$ and $R_2$ are each, H, said process comprising at least steps (I) to (II):

(I) reacting at least one compound selected from compounds of the formulae (IIa) and (IIb)

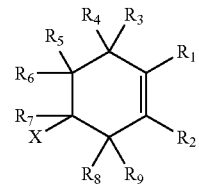

(IIa)

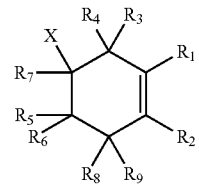

(IIb)

where X is a group selected from the group consisting of —CN, —CHO—, —CO$_2$R$_c$, —C(=O)R$_b$, —CONR$_c$ and —CH$_2$OH, where R$_b$ is selected from the group consisting of H and alkyl, and where R$_c$ is independently selected from the group consisting of H and alkyl;

with a gas mixture (G) comprising dinitrogen monoxide to obtain at least one compound selected from compounds of the formulae (IIIa), (IIIb), (IIIc) and (IIId)

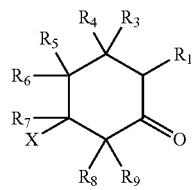
(IIIa)

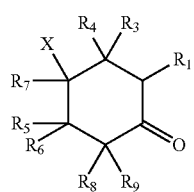
(IIIb)

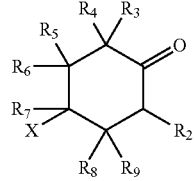
(IIIc)

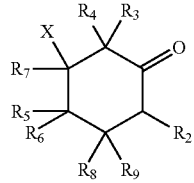
(IIId)

(II) converting the at least one compound obtained in step (I) to at least one compound selected from compounds of the formulae (Ia), (Ib), (Ic) and (Id).

A DETAILED DESCRIPTION OF THE INVENTION

In the context of the present application, "alkyl" means a linear, branched or cyclic C1 to C20 group which is optionally substituted by functional groups. Preferably, "alkyl" means a linear, branched or cyclic C1 to C9 group, further preferably a linear, branched or cyclic C1 to C5 group and more preferably a linear or branched C1 to C3 group, which is optionally substituted by functional groups. In the case that the alkyl group is substituted by a functional group, this functional group is preferably an aromatic radical. Examples of aromatic radicals are substituted or unsubstituted aryl radicals, for example benzyl, and substituted or unsubstituted heteroaryl radicals, alkyl-substituted aryl radicals or alkyl-substituted heteroaryl radicals. More preferably, "alkyl" in the context of the present application means methyl, ethyl, propyl or isopropyl, most preferably methyl.

Accordingly, the present invention also describes a process for preparing at least one cyclic diamine selected from diamines of the formulae (Ia), (Ib), (Ic) and (Id)

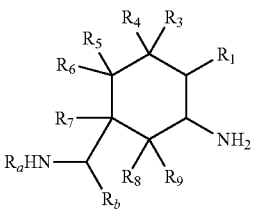
(Ia)

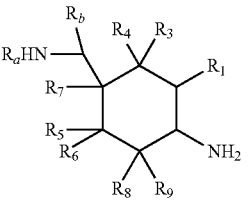
(Ib)

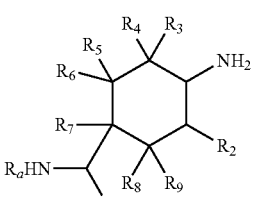
(Ic)

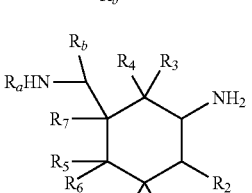
(Id)

where the $R_1$, $R_2$, $R_3$, $R_4$, $R_5$, $R_6$, $R_7$, $R_8$, $R_9$, $R_a$, $R_b$ radicals are each independently selected from the group consisting of H and alkyl;

and where $R_1$ or $R_2$ is, or $R_1$ and $R_2$ are each, H, methyl, ethyl, propyl and isopropyl;

said process comprising at least steps (I) to (II):

(I) reacting at least one compound selected from compounds of the formulae (IIa) and (IIb)

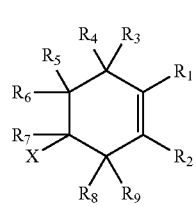
(IIa)

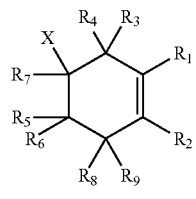
(IIb)

with a gas mixture (G) comprising dinitrogen monoxide to obtain at least one compound selected from compounds of the formulae (IIIa), (IIIb), (IIIc) and (IIId)

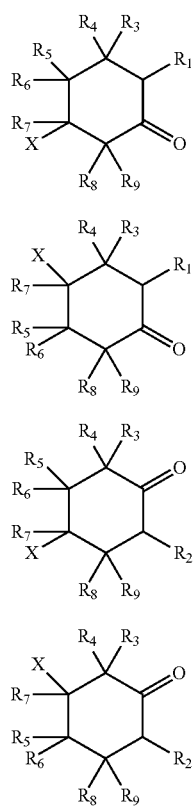

(II) converting the at least one compound obtained in step (I) to at least one compound selected from compounds of the formulae (Ia), (Ib), (Ic) and (Id).

The present invention likewise describes a diamine mixture obtainable by the process according to the invention, comprising at least one compound selected from compounds of the formulae (Ia), (Ib), (Ic) and (Id), where the $R_1$, $R_2$, $R_3$, $R_4$, $R_5$, $R_6$, $R_7$, $R_8$, $R_9$, $R_a$, $R_b$ radicals are each independently selected from the group consisting of H, methyl, ethyl, propyl and isopropyl; and where $R_1$ or $R_2$ is, or $R_1$ and $R_2$ are each, H. The present invention preferably describes a diamine mixture obtainable by the process according to the invention, comprising at least two compounds selected from compounds of the formulae (Ia), (Ib), (Ic) and (Id), where the $R_1$, $R_2$, $R_3$, $R_4$, $R_5$, $R_6$, $R_7$, $R_8$, $R_9$, $R_a$, $R_b$ radicals are each independently selected from the group consisting of H, methyl, ethyl, propyl and isopropyl; and where $R_1$ or $R_2$ is, or $R_1$ and $R_2$ are each, H.

According to the invention, X is a group selected from the group consisting of —CN, —CHO—, —$CO_2R_c$, —C(=O)$R_b$, —$CONR_c$ and —$CH_2OH$, where $R_b$, as already defined above, is selected from the group consisting of H and alkyl, and where $R_c$ is independently selected from the group consisting of H and alkyl, where, when X is —CN, —CHO—, —$CO_2R_c$, —$CONR_c$ or —$CH_2OH$, $R_b$ is preferably H.

Accordingly, the present invention also relates to a process as described above, wherein X is selected from the group consisting of —CN, —CHO, —$CO_2R_c$, —C(=O)$R_b$, —$CONR_C$ and —$CH_2OH$, where $R_b$ and $R_c$ are each independently selected from the group consisting of H and alkyl, where, when X is —CN, —CHO, —$CO_2R_c$, —C(=O)$R_b$, —$CONR_c$ or —$CH_2OH$, $R_b$ is preferably H.

X is preferably a group selected from the group consisting of —CN, —CHO—, —$CO_2R_c$, —C(=O)$R_b$, —$CONR_c$ and —$CH_2OH$, where $R_b$ is selected from the group consisting of H and alkyl, and where $R_c$ is independently selected from the group consisting of H and methyl.

The formulation "at least one compound selected from compounds of the formulae (IIa) and (IIb)" means, in the context of the present application, that either one compound of the formula (IIa) or one compound of the formula (IIb) or a mixture of the two compounds with dinitrogen monoxide is reacted.

The formulation "a compound of the formula (IIa)", as used in the context of the invention, includes mixtures of stereoisomers, for example cis/trans isomers, of the formula (IIa). It may likewise be only one stereoisomer. Accordingly, the formulation "a compound of the formula (IIb)", as used in the context of the invention, includes mixtures of stereoisomers, for example cis/trans isomers, of the formula (IIb). It may likewise be only one stereoisomer.

The formulation "to obtain at least one compound selected from compounds of the formulae (IIIa), (IIIb), (IIIc) and (IIId)" means in this connection that the reaction in step (I) forms either only one of the compounds mentioned, i.e., for example, either a compound of the formula (IIIa), or a compound of the formula (IIIb), or a compound of the formula (IIIc), or a compound of the formula (IIId), or a mixture comprising one of these compounds, or a mixture comprising two or three or four of these compounds, i.e., for example, a mixture comprising a compound of the formula (IIIa) and a compound of the formula (IIIb), or a mixture comprising a compound of the formula (IIIa) and a compound of the formula (IIIc), or a mixture comprising a compound of the formula (IIIa) and a compound of the formula (IIId), or a mixture comprising a compound of the formula (IIIb) and a compound of the formula (IIIc), or a mixture comprising a compound of the formula (IIIb) and a compound of the formula (IIId), or a mixture comprising a compound of the formula (IIIc) and a compound of the formula (IIId), or a mixture comprising a compound of the formula (IIIa) and a compound of the formula (IIIb) and a compound of the formula (IIIc), or a mixture comprising a compound of the formula (IIIa) and a compound of the formula (IIIb) and a compound of the formula (IIId) or a mixture comprising a compound of the formula (IIIa) and a compound of the formula (IIIc) and a compound of the formula (IIId), or a mixture comprising a compound of the formula (IIIb) and a compound of the formula (IIIc) and a compound of the formula (IIId), or a mixture comprising a compound of the formula (IIIa) and a compound of the formula (IIIb) and a compound of the formula (IIIc) and a compound of the formula (IIId), In the case that a mixture comprising three or four compounds selected from compounds of the formulae (IIIa), (IIIb), (IIIc) and (IIId) is obtained, $R_1$ and $R_2$ must both be H.

If, for example, a compound of the formula (IIa) is to be reacted with dinitrogen monoxide, at least one compound selected from compounds of the formulae (IIIa) and (IIIc) is obtained. In the case that compounds of the formulae (IIIa) and (IIIc), or a mixture comprising compounds of the formulae (IIIa) and (IIIc), are obtained, $R_1$ and $R_2$ are each H. When $R_1$ is alkyl and $R_2$ is H, the reaction of the compound of the formula (IIa) affords a compound of the formula (IIIa). When $R_1$ is H and $R_2$ is alkyl, the reaction in step (I) affords a compound of the formula (IIIc).

When, for example, a compound of the formula (IIb) is reacted with dinitrogen monoxide in step (I), at least one compound selected from compounds of the formulae (IIIb) and (IIId) is obtained. In the case that compounds of the formulae (IIIb) and (IIId), or a mixture comprising compounds of the formulae (IIIb) and (IIId), are obtained, $R_1$ and $R_2$ are each H. When $R_1$ is alkyl and $R_2$ is H, the reaction in step (I) affords a compound of the formula (IIIb). When $R_1$ is H and $R_2$ is alkyl, the reaction of the compound of the formula (IIb) in step (I) affords a compound of the formula (IIId).

The formulation "a compound of the formula is obtained" used in the context of the invention includes obtaining "mixtures comprising the compound of the formula", in which case the mixtures may further comprise by-products of the reaction and/or solvents and/or other assistants and/or other reagents. The formulation "a mixture comprising compounds of the formula is obtained" means accordingly that these mixtures may comprise by-products of the reaction and/or solvents and/or other assistants and/or other reagents. The by-products of the reaction and/or solvents and/or other assistants and/or other reagents are, if appropriate, removed in a suitable manner before step (II) as described below.

The formulation "a compound of the formula (IIIa)", as used in the context of the invention, includes mixtures of stereoisomers, for example cis/trans isomers, of the formula (IIIa). It may likewise be only one stereoisomer. The same applies to the formulations "a compound of the formula (IIIb)", "a compound of the formula (IIIc)" and "a compound of the formula (IIId)".

Whether a compound of the formula (IIa) or a compound of the formula (IIb) or a mixture of the two compounds with dinitrogen monoxide is reacted in step (I) depends, for example, on how the at least one compound which is selected from compounds of the formulae (IIa) and (IIb) and is used in step (I) is provided. According to the invention, this can be done in any manner known to those skilled in the art. Preference is given to preparing the at least one compound by a process comprising a Diels-Alder reaction. According to the substitution pattern and reaction conditions, the process affords either a compound of the formula (IIa) or a compound of the formula (IIb) or a mixture of a compound of the formula (IIa) and a compound of the formula (IIb).

A Diels-Alder reaction is generally understood to mean a reaction in which a double or triple bond in a dienophile reacts in a 1,4 mechanism with a conjugated diene. Diels-Alder reactions are described, for example, in V. P. Krivonogov, G. A. Tolstikov, D. N. Lazareva, V. A. Davydova, F. S. Zarudii, I. Krivonogova, Y. I. Murinov, Yu. *Pharm. Chem. J.* (Engl. Transl.) 2001, 35, 26-29; *Khim. Farm. Zh.* 2001, 35, 2528, M. B. Korzenski, J. W. Kolis, *Tetrahedron Lett.* 1997, 38, 5611-5614; J. Beger, F. Meier, *J. Prakt. Chem.* 1980, 322, 69-80; T. R. Kelly, S. K. Maity, P. Meghani, N. S. Chandrakumar, *Tetrahedron Lett.* 1989, 30, 1357-1360; Patent; I. G. Farbenind.; U.S. Pat. No. 2,262,002; 1939; Patent; I. G. Farbenind.; DE 710131; 1938; S. Petrow, *Zh. Obshch. Khim.* 1947, 17, 2231; *Chem. Abstr.* 1948, 4957; R. Doucet, *Bull. Soc. Chim. Fr.* 1954, 610-612; Patent; Wingfoot Corp.; U.S. Pat. No. 2,217,632; 1939; Ziegler et al., *Justus Liebigs Ann. Chem.* 1954, 589, 91-106; P. Pistor, *Justus Liebigs Ann. Chem.* 1949, 562, 239-244; J. Beger, F. Meier, *J. Prakt. Chem.* 1980, 322, 69-80; and in D. Janz, *J. Am. Chem. Soc.* 1953, 75, 5389-5390.

In the context of the invention, a Diels-Alder reaction is understood to mean the reaction of a compound of the formula (ia) with a compound of the formula (ib).

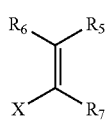

(ia)

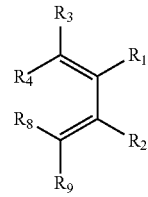

(ib)

Accordingly, the present invention relates to a process in which the at least one compound which is selected from compounds of the formulae (IIa) and (IIb) and is used in step (I) is provided by a process comprising at least step (I):
(i) reacting a compound of the formula (ia)

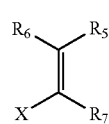

(ia)

with a compound of the formula (ib)

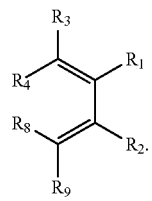

(ib)

As already described above, the $R_1$, $R_2$, $R_3$, $R_4$, $R_5$, $R_6$, $R_7$, $R_8$ and $R_9$ radicals are each independently selected from the group consisting of H and alkyl, where $R_1$ or $R_2$ is, or $R_1$ and $R_2$ are each, H, and where X is selected from the group consisting of —CN, —CHO—, —CO$_2$R$_c$, —C(=O)R$_b$, —CONR$_c$ and —CH$_2$OH, where R$_b$ and R$_c$ are each independently selected from the group consisting of H and alkyl, where, when X is —CN, —CHO—, CO$_2$R$_c$, —C(=O)R$_b$, —CONR$_c$ or —CH$_2$OH, R$_b$ is preferably H.

In particularly preferred embodiments, X is selected from the group consisting of —CN, —CHO—, —CO$_2$R$_c$, —C(=O)R$_b$, —CONR$_c$ and —CH$_2$OH, where R$_b$ and R$_c$ are each independently selected from the group consisting of H and alkyl, preferably where R$_b$ and R$_c$ are each H, and where $R_5$ and $R_6$ are each H and $R_7$ is methyl; or where X is selected from the group consisting of —CN, —CHO—, —CO$_2$R$_c$, —C(=O)R$_b$, —CONR$_c$ and —CH$_2$OH, where R$_b$ and R$_c$ are each independently selected from the group consisting of H and alkyl, where, preferably, R$_b$ and R$_c$ are each H, and where $R_5$ is methyl and $R_6$ and $R_7$ are each H; or where X is selected from the group consisting of —CN, —CHO—, —CO$_2$R$_c$, —C(=O)R$_b$, —CONR$_c$ and —CH$_2$OH, where R$_b$ and R$_c$ are each independently selected from the group consisting of H and alkyl, and preferably where R$_b$ and R$_c$ are each H, and where $R_6$ is methyl and $R_5$ and $R_7$ are each H; or where X is selected from the group consisting of —CN, —CHO—, —CO$_2$R$_c$, —C(=O)R$_b$, —CONR$_c$ and —CH$_2$OH, where R$_b$ and R$_c$ are each independently selected from the group consisting of H and alkyl, preferably where R$_b$ and R$_c$ are each H, and where $R_5$, $R_6$ and $R_7$ are each H.

More preferably, the compound of the formula (ib) used is a compound selected from the group consisting of methacrylonitrile, acrylonitrile, acrolein, methacrolein, acrylic acid, methacrylic acid, crotonaldehyde, crotonitrile, crotonic acid, methyl acrylate, methyl methacrylate and methyl crotonate. Very particular preference is given to using acrylonitrile or methacrylonitrile.

In the context of the invention, the compounds of the formula (ib) used are especially compounds in which $R_2$, $R_3$, $R_4$, $R_8$ and $R_9$ are each H and $R_1$ is methyl, or $R_1$, $R_3$, $R_4$, $R_8$ and $R_9$ are each H and $R_2$ is methyl, or $R_1$, $R_2$, $R_8$ and $R_9$ are each H and $R_3$ and $R_4$ are each methyl.

In a particularly preferred embodiment, $R_1$, $R_2$, $R_3$, $R_4$, $R_8$ and $R_9$ are each H.

In a preferred embodiment of the present invention, the at least one compound selected from compounds of the formulae (IIa) and (IIb) is provided by reacting a compound of the formula (Ia) in which X is selected from the group consisting of —CN, —CHO—, —$CO_2R_c$, —C(=O)$R_b$, —$CONR_c$ and —$CH_2OH$, where $R_b$ and $R_c$ are each independently selected from the group consisting of H and alkyl, and in which $R_5$, $R_6$ and $R_7$ are each H, with a compound of the formula (ib) where $R_1$, $R_2$, $R_3$, $R_4$, $R_8$ and $R_9$ are each H. Further preferably, the at least one compound selected from compounds of the formulae (IIa) and (IIb) is provided by reacting a compound of the formula (ia) in which X is selected from the group consisting of —CN, —CHO—, —$CO_2R_c$, —C(=O)$R_b$, —$CONR_c$ and —$CH_2OH$, where $R_b$, $R_c$, $R_5$, $R_6$ and $R_7$ are each H, with a compound of the formula (ib) where $R_1$, $R_2$, $R_3$, $R_4$, $R_8$ and $R_9$ are each H. More preferably, the at least one compound selected from compounds of the formulae (IIa) and (IIb) is provided by reacting a compound of the formula (ia) in which is X —CN and $R_5$, $R_6$ and $R_7$ are each H with a compound of the formula (ib) where $R_1$, $R_2$, $R_3$, $R_4$, $R_8$ and $R_9$ are each H.

The present invention accordingly describes a process as described above, in which the at least one compound which is selected from compounds of the formulae (IIa) and (IIb) and is used in step (I) is provided by a process comprising at least step (i):
(i) reacting a compound of the formula (ia) where X is selected from the group consisting of —CN, —CHO, —$CO_2R_c$, —C(=O)$R_b$, —$CONR_c$ and —$CH_2OH$, where $R_b$ and $R_c$ are each independently selected from the group consisting of H and alkyl, and where $R_5$, $R_6$ and $R_7$ are each H with a compound of the formula (ib) where $R_1$, $R_2$, $R_3$, $R_4$, $R_8$ and $R_9$ are each H.

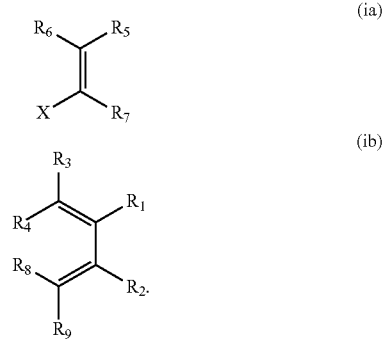

In an alternative embodiment of the present invention, the at least one compound selected from compounds of the formulae (IIa) and (IIb) is provided by reacting a compound of the formula (ia) in which $R_5$ and $R_6$ are each H and $R_7$ is methyl and in which X is selected from the group consisting of —CN, —CHO—, —$CO_2R_c$, —C(=O)$R_b$, —$CONR_c$ and —$CH_2OH$, where $R_b$ and $R_c$ are each independently selected from the group consisting of H and alkyl, preferably where $R_b$ and $R_c$ are each H, especially in which X is —CN, with a compound of the formula (ib) where $R_1$, $R_2$, $R_8$, $R_5$ and $R_9$ are each H and $R_3$, $R_5$ and $R_7$ are each methyl.

The present invention accordingly describes a process as described above, in which the at least one compound which is selected from compounds of the formulae (IIa) and (IIb) and is used in step (i) is provided by a process comprising at least step (i):
(i) reacting a compound of the formula (ia) where X is selected from the group consisting of —CN, —CHO, —$CO_2R_c$, —C(=O)$R_b$, —$CONR_c$ and —$CH_2OH$, where $R_b$ and $R_c$ are each independently selected from the group consisting of H and alkyl, and $R_5$ and $R_6$ are each H and $R_7$ is methyl, with a compound of the formula (ib) where $R_1$, $R_2$, $R_8$ and $R_9$ are each H and $R_3$ and $R_4$ are each methyl.

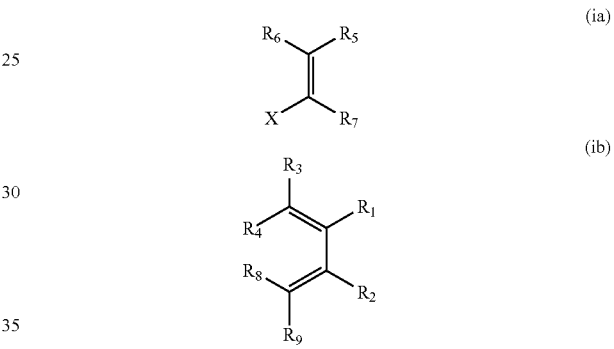

The reaction of stage (i) can generally be effected by all process regimes known to those skilled in the art from the prior art for this reaction. It can be carried out, for example, without catalyst or in the presence of a Lewis acid.

Preference is given to effecting the reaction thermally at temperatures in the range from 20° C. to 200° C., further preferably at temperatures in the range from 60° C. to 180° C., further preferably at temperatures in the range from 80° C. to 160° C. and more preferably at temperatures in the range from 110° C. to 140° C. Typically, the reaction is effected under ambient pressure or under autogenous pressure of the reaction system, for example at a pressure of from 1 to 10 bar, preferably from 1 to 5 bar.

The present invention accordingly also relates to a process as described above, wherein the reaction in step (i) is effected at a temperature in the range from 20° C. to 200° C.

The reaction in step (i) is typically performed in a solvent, but can also be effected directly by heating the components. Suitable solvents are especially aliphatic, cycloaliphatic, aromatic and alkyl-substituted aromatic hydrocarbons. Among the aliphatic hydrocarbons, particular preference is given to branched and unbranched hydrocarbons having from 6 to 12 carbon atoms, especially from 6 to 10 carbon atoms, i.e. hexanes, heptanes, octanes and decanes, and mixtures of such hydrocarbons. Among the cycloaliphatic hydrocarbons, particular emphasis should be given to cyclohexane and terpene hydrocarbons. From the group of the aromatics and alkyl-substituted aromatics, benzene and methylated benzenes such as toluene, xylenes, trimethylbenzenes, tetramethylbenzenes and mixtures of such methylated benzenes are particularly suitable; instead of methyl groups or in addition, the benzene ring may also have other lower alkyl groups, such as ethyl, n-propyl and isopropyl. Particular preference is given to using toluene as the solvent.

The present invention accordingly also relates to a process as described above wherein the reaction in step (i) is effected in a mixture at least comprising the compound of the formula (ia), the compound of the formula (ib) and toluene, In addition to the solvent, the mixture for the reaction may comprise further assistants, such as Lewis acids, e.g. boron trifluoride.

The reaction in (i) affords, as described above, at least one compound of the formula (IIa) and/or (IIb). As stated above, this formulation also includes obtaining a mixture comprising the compound of the formula (IIa) and/or (IIb). When the mixtures, as well as the at least one compound, also comprise further constituents such as unconverted compound (ia) and/or (ib), and/or by-products and/or solvents and/or other assistants and/or other reagents, the further constituents may, if appropriate, be removed in a suitable manner before step (I). It is possible to remove only a portion of the further constituents, or essentially all further constituents. For example, it is possible to remove unconverted compounds (ia) and/or (ib) if present and to reuse them in step (i). It is equally possible to remove solvents, if used, from the at least one compound selected from compounds of the formulae (Ia) and (Ib), and at least a portion of the solvent removed can, if appropriate, be used again in step (i).

If appropriate, the unconverted compound(s) (ia) and (ib) can be removed together with the solvent and recycled together, if appropriate after further workup steps, into step (i).

To remove the further constituents from the at least one compound, i.e. from (IIa) and/or (IIb), it is generally possible to use all processes known for this purpose to those skilled in the art, for example at least one distillation, at least one sublimation or at least one crystallization.

Preference is given to distilling the mixture obtained in step (i) before step (I). The distillation is performed in the manner known per se to those skilled in the art.

The present invention accordingly also provides a process as described above, in which the at least one compound which is selected from compounds of the formulae (IIa) and (IIb) and is used in step (I) is provided by a process as described above, which further comprises at least step (ii):

(ii) distilling the mixture obtained from the reaction in (i).

The reaction of the at least one compound which is selected from compounds of the formulae (IIa) and (IIb) and is provided if appropriate by means of a process comprising at least one step (i) with dinitrogen monoxide in stage (I) can generally be effected by all process regimes in which at least one compound selected from compounds of the formulae (IIIa), (IIIb), (IIIc) and (IIId) is obtained.

For the reaction in step (I), at least one suitable solvent or diluent can be used. In general, the addition of a solvent or diluent is unnecessary in the reaction in step (I), but preference is given to using at least one solvent or diluent. Examples of such solvents and diluents include cyclic alkanes, for example cyclododecane or cyclodecanone, or saturated aliphatic or aromatic, optionally alkyl-substituted hydrocarbons, essentially all common solvents and/or diluents being suitable, with the proviso that they have neither a C—C double bond nor an aldehyde group. Preference is given to cyclopentane, hexane, octane, decane, dodecane or benzene, or alkylbenzenes, for example toluene, xylenes, ethylbenzene, or ethers, for example methyl tert-butyl ether, tetrahydrofuran, diethyl ether, or esters, for example methyl acetate, ethyl acetate, methylbenzoate, or nitriles, for example acetonitrile, benzonitrile, or alcohols, for example butanol, 2-ethylhexanol, ethanol or phenols, for example phenol, cresols, or amines, for example aniline, triethylamine, N,N-dimethylaniline, or mixtures of two or more of the compounds mentioned or two or more compounds from the classes mentioned. Particular preference is given to using at least toluene for the reaction in step (i).

The reaction in step (I) is effected preferably at temperatures in the range from 100 to 350° C., further preferably at temperatures in the range from 140 to 320° C., further preferably at temperatures in the range from 170 to 290° C. and more preferably at temperatures in the range from 200 to 265° C.

The present invention accordingly also relates to a process as described above, wherein the reaction in step (1) is effected at temperatures in the range from 200 to 265° C., It is possible to alter the temperature in the course of the reaction in step (I). It is possible in this context to perform the reaction at two or more temperatures or within two or more temperature ranges, each of which is within the limits specified above. Temperature changes in the course of the reaction can be conducted continuously or discontinuously.

The reaction in step (I) is preferably effected at pressures which are higher than the autogenous pressure of the reactant or product mixture at the selected reaction temperature or at the selected reaction temperatures. Preference is given to effecting the reaction in step (I) at a pressure in the range from 1 to 100 bar, preferably within a range from 10 to 80 bar, further preferably within a range from 20 to 60 bar and more preferably within a range from 30 to 55 bar.

The present invention accordingly also relates to a process as described above, wherein the reaction in step (I) is effected at a pressure in the range from 30 to 55 bar.

It is possible to perform the reaction in step (I) at two or more pressures or within two or more pressure ranges, each of which is within the limits specified above.

As far as the gas mixture (G) used in step (I) is concerned, the gas mixture (G) used may in principle be any gas mixture comprising dinitrogen monoxide. The term "gas mixture" as used in the present invention refers to a mixture of two or more compounds which are in the gaseous state under ambient pressure and ambient temperature. In the case of an altered temperature and/or altered pressure, the gas mixture may also be present in a different state of matter, for example in liquid or supercritical form, and is still referred to as a gas mixture in the context of the present invention. The dinitrogen monoxide may in principle originate from any desired source. It is equally suitable to dissolve the gas mixture in a solvent and to use it in step (I).

In a preferred embodiment, a gas mixture (G) comprising at least 20% by volume of dinitrogen monoxide is used, preference being given in turn to using mixtures with a dinitrogen monoxide content in the range of at least 40% by volume, further preferably in the range of at least 60% by volume, further preferably in the range of at least 80% by volume, for example of from at least 80% by volume to 99.99% by volume.

In the context of the present invention, the composition of the gas mixtures or of the liquefied gas mixtures is reported in % by volume, These figures are based on the composition of the gas mixtures at ambient pressure and ambient temperature.

As well as dinitrogen monoxide, the gas mixture (G) may also comprise at least one further gas. Essentially all gases are conceivable in this context, provided that it is ensured that the reaction in step (I) is possible. Should the gas mixture also comprise at least one further gas, preference is given especially to mixtures which, as well as dinitrogen monoxide, comprise at least one inert gas. The term "inert gas" as used in the context of the present invention refers to a gas which behaves inertly with regard to the reaction of dinitrogen monoxide with the at least one compound in step (I). Examples of inert gases include nitrogen, carbon dioxide, carbon monoxide, argon, methane, ethane and propane.

It is likewise possible for the mixture also to comprise gases which do not behave as inert gases in the reaction in (I). Such gases include $NO_x$ or, for example, oxygen. The term "$NO_x$", as understood in the context of the present invention, refers to all compounds $N_aO_b$ apart from dinitrogen monoxide ($N_2O$) where a is 1 or 2 and b is from to 6 . Instead of the term "$NO_x$", the term "nitrogen oxides" is also used in the context of the present invention. In such a case, preference is given to using those gas mixtures (G) whose content of these gases is at most 1% by volume, preferably at most 0.5% by volume, based on the total weight of the gas mixture (G).

In principle, the composition of the mixtures, in the context of the present invention, can be determined in any manner known to those skilled in the art, In the context of the present invention, the composition of the gas mixtures (G) is determined by gas chromatography. However, it can also be determined by means of UV spectroscopy or IR spectroscopy or by wet-chemical means.

For the purposes of the process according to the invention, the dinitrogen monoxide can be prepared selectively for use in the process. Preference is given, among other methods, to preparation via the thermal decomposition of $NH_4NO_3$, as described, for example, in US 3,656,899 , whose content on this subject is incorporated fully into the context of the present application by reference. Likewise preferred is additionally preparation via the catalytic oxidation of ammonia, as described, for example, in U.S. Pat. No. 5,849,257 or in WO 98/25698 , whose content on this subject is Incorporated fully into the context of the present application by reference.

Particular preference is given to using, as the gas mixture (G) which comprises dinitrogen monoxide, an offgas from an industrial process. According to the invention, it is also possible to use mixtures of different offgases, for example mixtures of two or three different offgases.

The present invention accordingly also describes a process as described above, wherein the gas mixture (G) at least comprising dinitrogen monoxide is the offgas of an industrial process.

The offgas comprising dinitrogen monoxide preferably originates from an adipic acid plant, a dodecanedioic acid plant, a hydroxylamine plant and/or a nitric acid plant, the latter in turn preferably being operated with at least one offgas of an adipic acid plant, of a dodecanedioic acid plant or of a hydroxylamine plant.

According to the invention, it is possible to purify or to concentrate the gas mixture (G) before use in the reaction in step (I). A suitable purification process comprises, for example, the absorption of the gas mixture in an absorbent, for example in an organic solvent or water, and the subsequent desorption from the laden absorbent.

Preference is given to performing step (I) of the process according to the invention in a reactor. There are no particular restrictions for the reactors usable for this purpose. In particular, the reaction can be effected in batchwise mode or in continuous mode.

Accordingly, for example, the reactors used may be at least one CSTR (Continuous Stirred Tank Reactor) with at least one internal and/or at least one external heat exchanger, at least one tubular reactor, at least one tube bundle reactor or at least one loop reactor. It is likewise possible to configure at least one of these reactors such that it has at least two different zones. Such zones may differ, for example, in terms of reaction conditions, for example the temperature or the pressure, and/or in terms of the geometry of the zones, for example the volume or the cross section. When the reaction is performed in two or more reactors, it is possible to use two or more identical reactor types or at least two different reactor types.

Preference is given to performing the reaction in step (I) in a single reactor.

When the reaction is performed continuously, the residence time of the reactants in the at least one reactor in the reaction in step (I) is generally in the range from 0.1 up to 50 h, preferably in the range from 0.2 to 25 h and more preferably in the range from 0.25 to 10 h.

As far as the quantitative ratio of the at least one compound of the formula (IIa) and/or (IIb) to dinitrogen monoxide is concerned, it is preferably within a range from 0.001 to 0.01 , preferably within a range from 0.01 to 0.1 and more preferably within a range from 0.1 to 1.

The at least one compound obtained in step (I), which has if appropriate been subjected to at least one intermediate treatment as described above, is converted to at least one compound selected from compounds of the formulae (Ia), (Ib), (Ic) and (Id) in step (II) preferably by reductive amination.

The term "reductive amination" as used in the context of the invention means a substitution in which at least one oxo compound is converted to at least one amine compound.

What is meant by the term "at least one oxo compound" is the compound which is selected from compounds of the formulae (IIIa), (IIIb), (IIIc) and/or (IIId), is obtained in step (I) and comprises at least one keto function as a result of the reaction in step (I).

The term "the compound obtained in step (I)" comprises the compound(s) obtained from the reaction in step (I), and the compound(s) which have been obtained from the reaction in step (I) and has/have, if appropriate, as described above, been subjected to at least one intermediate treatment, In the reductive amination in step (II), according to the invention, the at least one compound which is selected from compounds of the formulae (IIIa), (IIIb), (IIIc) and/or (IIId) and is obtained in step (I) is reacted with an amine compound $NH_2R_a$ to give the corresponding at least one imine compound, and the at least one reaction product of the imine formation is hydrogenated using hydrogen. Particular preference is given to effecting the reductive amination in the context of the invention using ammonia.

In the reaction with the amine compound $NH_2R_a$, the functional X group of the at least one compound which is selected from compounds of the formulae (IIIa), (IIIb), (IIIc) and/or (IIId) and is obtained in step (I) is, if appropriate, modified with the amine. The hydrogenation subsequently converts the —X group, which may have been modified with the amine, to the

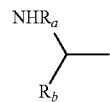

group. When X is CN, the X group is reduced to $CH_2NH_2$, i.e. $R_a$ and $R_b$ are each H. When the X group is a group selected from the group consisting of —CHO—, —$CO_2R_c$ and —$CH_2OH$, X is preferably reduced to $CH_2NHR_a$, i.e. $R_b$ is H.

When X is —CONR$_c$, the X group is reduced to CH$_2$NHR$_a$, R$_c$ in this case preferably being selected such that R$_c$ is the same as R$_a$.

More preferably, R$_a$ is H; the reaction in step (II) is accordingly preferably effected with ammonia.

The present invention accordingly also describes a diamine mixture obtainable by the process according to the invention, comprising at least one compound selected from compounds of the formulae (Ia), (Ib), (Ic) and (Id), where the R$_1$, R$_2$, R$_3$, R$_4$, R$_5$, R$_6$, R$_7$, R$_8$, R$_9$, R$_b$ radicals are each independently selected from the group consisting of H, methyl, ethyl, propyl and isopropyl; and where R$_a$ is H, and where R$_1$ or R$_2$ is, or R$_1$ and R$_2$ are each, H. Alternatively, the present invention describes a diamine mixture obtainable by the process according to the invention, comprising at least two compounds selected from compounds of the formulae (Ia), (Ib), (Ic) and (Id), where the R$_1$, R$_2$, R$_3$, R$_4$, R$_5$, R$_6$, R$_7$, R$_8$, R$_9$, R$_b$ radicals are each independently selected from the group consisting of H, methyl, ethyl, propyl and isopropyl; and where R$_a$ is H, and where R$_1$ or R$_2$ is, or R$_1$ and R$_2$ are each, H.

The present invention preferably also describes a diamine mixture obtainable by the process according to the invention, comprising at least one compound selected from compounds of the formulae (Ia), (Ib), (Ic) and (Id), where the R$_1$, R$_2$, R$_3$, R$_4$, R$_5$, R$_6$, R$_7$, R$_8$, R$_9$, R$_a$ and R$_b$ radicals are each H. Alternatively, the present invention describes a diamine mixture obtainable by the process according to the invention, comprising at least two compounds selected from compounds of the formulae (Ia), (Ib), (Ic) and (Id), where the R$_1$, R$_2$, R$_3$, R$_4$, R$_5$, R$_6$, R$_7$, R$_6$, R$_9$, R$_a$ radicals are each and R$_b$ is.

In an alternative embodiment, the present invention also describes a diamine mixture obtainable by the process according to the invention, comprising at least one compound selected from compounds of the formulae (Ia), (Ib), (Ic) and (Id), where the R$_1$, R$_2$, R$_5$, R$_6$, R$_8$, R$_9$, R$_a$ R$_b$ radicals are each H, and R$_3$, R$_4$ and R$_7$ are each methyl. Alternatively, the present invention describes a diamine mixture obtainable by the process according to the invention, comprising at least two compounds selected from compounds of the formulae (Ia), (Ib), (Ic) and (Id), where the R$_1$, R$_2$, R$_5$, R$_6$, R$_8$, R$_9$, R$_a$ and R$_b$ radicals are each H and R$_3$, R$_4$, R$_7$ are each methyl.

The reaction in step (II) can be effected in one or more stages, for example in two stages, i.e. the imine formation and the hydrogenation can be carried out in one stage or else in a plurality of stages. In addition, the reaction can be carried out in the presence of a single catalyst or in the presence of at least two catalysts. When, for example, two catalysts are used, one catalyst preferably catalyzes the imine formation and the other catalyst the hydrogenation.

Particularly in cases in which an insufficient conversion and/or undesired by-products, for instance as a result of direct hydrogenation of the at least one oxo compound, are obtained in a one-stage method using a single catalyst, it may be advantageous to perform step (II), preferably the reductive amination, in two stages, The prior art discloses both one-stage and two-stage processes for preparing cyclic diamines from cyclic oxo compounds. For example, EP 0 659 734 describes a one-stage process for preparing isophoronediamine from isophoronenitrile. A two-stage process for converting isophoronenitrile to isophoronediamine is described, for example, in EP 0 042 119 . The imination catalyst used is an inorganic or organic ion exchanger in the ammonium form. A two-stage process for converting isophoronenitrile to isophoronediamine is likewise described by EP 0 816 323 . Here, an organopolysiloxane is used as the imination catalyst, and an activated cobalt catalyst for the hydrogenation.

In the context of the invention, the reaction in step (II) is preferably effected in two stages. Accordingly, the present invention also relates to a process as described above, wherein the conversion in step (II) comprises at least steps (a) and (b):
(a) contacting the at least one compound selected from compounds of the formula (IIIa), (IIIb), (IIIc), (IIId), with an amine compound NH$_2$R$_a$, preferably ammonia,
(b) hydrogenating the at least one compound obtained in step (a).

The contacting in (a) can be carried out in the presence of at least one catalyst, for example in the presence of one, two or three different catalysts. If, in step (a), a catalyst is to be used, preference is given to using exactly one catalyst. The catalysts used here may generally be all imination catalysts known to those skilled in the art from the prior art for such reactions. For example, the catalysts used may be those described in EP 0 659 734 , EP 0 042 119 , EP 0 449 089 or EP 0819 323 A2 . Particular preference is given in accordance with the invention to aluminum oxide and titanium oxide.

The contacting in step (a) can be effected batchwise or continuously, using customary reactors, for example tubular reactors or stirred tanks. Preference is given to effecting the process in tubular reactors with continuous flow.

In one embodiment, in which a catalyst is used, the catalyst can be used either in the form of a suspended catalyst or in the form of a fixed bed arranged in a reactor. Preference is given to arranging the catalyst in a fixed bed. The substance mixture to be converted can also either be fed to the fixed bed catalyst from the bottom, and hence the reactor can be kept flooded, or the reactor is operated as a trickle bed by introducing the substance mixture at the top.

In an alternative embodiment, the reaction in step (a) is effected without catalyst.

The contacting in step (a) is effected preferably at temperatures in the range from 0° C. to 150° C., further preferably at temperatures in the range from 10° C. to 120° C., further preferably at temperatures in the range from 20 to 100° C., further preferably from 50 to 90° C. When a catalyst is used, the reaction is effected, for example, at from 40 to 80° C.

The present invention accordingly also relates to a process as described above, wherein the contacting in step (a) is effected at a temperature in the range from 0 to 150° C.

The amount of amine compound NH$_2$R$_a$ used, especially of ammonia, in step (II), or, in the case that step (II) comprises at least stages (a) and (b), in step (a), is preferably in the range from 1 to 80 equivalents, further preferably in the range from 2 to 60 equivalents, further preferably in the range from 2 to 50 equivalents and more preferably in the range from 5 to 40 equivalents, based on the total number of moles of the at least one compound selected from compounds of the formulae (IIIa), (IIIb), (IIIc) and (IIId).

According to the invention, step (II) can be performed in the presence of a solvent. Preferred solvents are alcohols, such as methanol, ethanol, propanol, ethylene glycol and ethylene glycol monomethyl ether, ethers such as diethyl ether, tetrahydrofuran, dioxane and ethylene glycol dimethyl ether, hydrocarbons such as hexane and heptane, and mixtures of the solvents mentioned.

In a preferred embodiment of the invention, the conversion of the at least one compound which is selected from compounds of the formulae (IIIa), (IIIb), (IIIc) and/or (IIId) and is obtained in step (I) to at least one compound selected from compounds of the formulae (Ia), (Ib), (Ic) and (Id) in step (II) is effected in the presence of methanol. In this case, a mixture comprising methanol and the at least one compound selected from compounds of the formulae (Ia), (Ib), (Ic) and (Id) is preferably obtained.

When solvent is used in step (II), preference is given to using an amount In the range from 5 to 95% by weight, further preferably in the range from 10 to 80% by weight, further preferably in the range from 15 to 70% by weight and more preferably in the range from 20 to 50% by weight, based on the total weight of the at least one compound selected from compounds of the formulae (IIIa), (IIIb), (IIIc) and (IIId).

The present invention accordingly also describes a process for preparing at least one cyclic diamine selected from diamines of the formulae (Ia), (Ib), (Ic) and (Id)

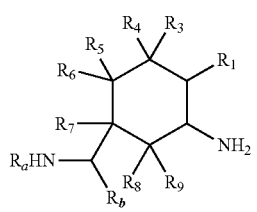
(Ia)

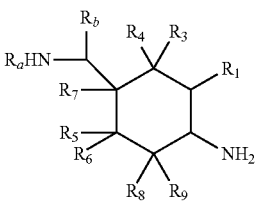
(Ib)

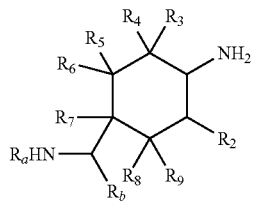
(Ic)

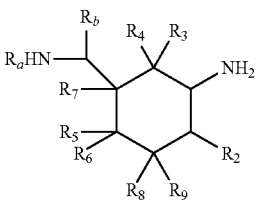
(Id)

where the $R_1$, $R_2$, $R_3$, $R_4$, $R_5$, $R_6$, $R_7$, $R_8$, $R_9$, $R_a$, $R_b$ radicals are each independently selected from the group consisting of H and alkyl;

and where $R_1$ or $R_2$ is, or $R_1$ and $R_2$ are each, H, said process comprising at least steps (I) to (II):

(I) reacting at least one compound selected from compounds of the formulae (IIa) and (IIb)

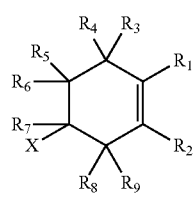
(IIa)

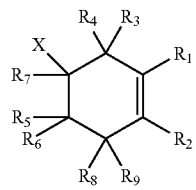
(IIb)

with a gas mixture (G) comprising dinitrogen monoxide to obtain at least one compound selected from compounds of the formulae (IIIa), (IIIb), (IIIc) and (IIId)

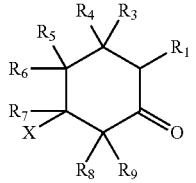
(IIIa)

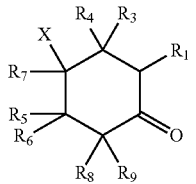
(IIIb)

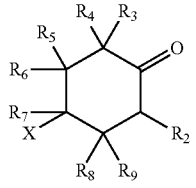
(IIIc)

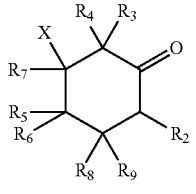
(IIId)

(II) reacting a mixture Comprising methanol and the at least one compound obtained in step (I) with an amine compound $NH_2R_a$, especially with ammonia, to give at least one compound selected from compounds of the formulae (Ia), (Ib), (Ic) and (Id).

The present invention accordingly also describes a process, as described above, wherein the reaction in (II) comprises at least steps (a) and (b):

(a) contacting a mixture comprising methanol and at least one compound selected from compounds of the formula (IIIa), (IIIb), (IIIc), and (IIId), with an amine compound $NH_2R_a$, especially with ammonia, (b) hydrogenating the at least one compound obtained in step (a).

The reaction pressure in stage (a) is preferably within the range from 1 to 300 bar, further preferably within the range from 10 to 250 bar, further preferably within the range from 30 bar to 250 bar.

For the hydrogenation in (b), it is possible to use customary hydrogenation catalysts, as are common knowledge for the hydrogenation of imines and for the hydrogenation of any other reducing groups present in the oxo compound. Preference is given to using at least one catalyst comprising cobalt, nickel, ruthenium and/or other noble metals. Examples of such catalysts are specified in the documents cited above. The hydrogenation catalyst can also be used in the form of a suspended catalyst or fixed bed catalyst. The hydrogenation can be effected, for example, in trickle bed mode.

According to the invention, catalysts comprising Raney nickel and Raney cobalt and Raney nickel or cobalt catalysts are preferred as hydrogenation catalysts. In particular, a catalyst comprising Raney cobalt is used.

The present invention accordingly also relates to a process as described above, wherein the hydrogenation in step (b) is effected over a catalyst comprising Raney cobalt.

Particular preference is given to Raney cobalt catalysts doped with other metals, especially with chromium, nickel, iron and/or cobalt.

The present invention accordingly also relates to a process as described above, wherein the catalyst is doped with chromium, nickel, iron and/or cobalt.

The Raney catalysts can be obtained in a known manner from alloys of nickel or cobalt with aluminum and/or Zn, Mg, Si and possibly the doping elements, by leaching out the aluminum and/or the Zn, Mg, Si, leaching usually being effected with alkali solutions.

It is likewise possible to use cocatalysts. For example, salts of Ni, Co, Y, La, Ce are used. Useful anions of the salts include those of the mineral acids, especially sulfuric acid and hydrochloric acid, but also of the carboxylic acids. Halides, especially chlorides, of the metals Mentioned are very suitable. If cocatalysts are used, the amount of cocatalysts used is appropriately, per mole of catalyst, calculated as Co or Ni, from 0.01 to 0.5 mol, especially from 0.05 to 0.2 mol.

The hydrogenation in step (b) is effected preferably at temperatures in the range from 0° C. to 350° C., further preferably at temperatures in the range from 10° C. to 200° C., further preferably at temperatures in the range from 20 to 180° C., further preferably at temperatures in the range from 50 to 150° C. The reaction pressure in stage (b) is preferably within the range from 1 to 300 bar, further preferably within the range from 10 to 250 bar, further preferably within the range from 30 bar to 250 bar.

The present invention accordingly also relates to a process as described above, wherein the hydrogenation in (b) is effected at a temperature in the range from 50 to 150° C. and a pressure in the range from 1 to 300 bar.

After the hydrogenation has ended, the reaction mixture is worked up in a manner known per se. Customarily, the steps are releasing the pressure, evaporating off the ammonia, if appropriate removing insoluble constituents from the solution, distillatively removing the solvent and fractionally distilling the compound selected from compounds of the formulae (Ia), (Ib), (Ic) and (Id) under reduced pressure.

The at least one cyclic diamine obtained in accordance with the invention is preferably used to prepare polyaddition resins from the group of the epoxy resins, polyurethane resins and polyurea resins.

The invention is illustrated in detail in the examples which follow.

EXAMPLES

Example 1

Preparation of 3-cyclohexenecarbonitrile

Acrylonitrile (800 g, 15.1 mol, purity >99%) was sucked from a laboratory bottle into a nitrogen-inertized and subsequently evacuated 3.5 l autoclave with overhead stirrer (2×6 stirrer blades). The bottle was, if appropriate, filled with toluene (200 g) which was sucked into the autoclave by the same path. 1,3-Butadiene (purity >99.5%) was injected at a pressure of 30 bar up to a concentration c. The stirring was adjusted to 1000 rpm and the autoclave was heated up to a temperature T. After t hours, the autoclave was cooled to 40° C. and then decompressed to ambient pressure. With the stirrer running, 250 l (STP) of $N_2$/h were introduced via a riser tube for 3 h in order to drive out the unconverted 1,3-butadiene. Volatile fractions were removed under reduced pressure (70 mbar, distillation temperature 50° C.). Distillation of the residue under reduced pressure (30 mbar, 100° C.) gave 3-cyclohexenecarbonitrile as a colorless liquid of >99% purity. The results of the tests are shown in table 1.

TABLE 1

| Ex. | T [° C.] | t [h] | Solv. | c (acrylonitrile) [M] | C (%)[b] | S (%)[c] |
|---|---|---|---|---|---|---|
| 1.1 | 100 | 1 | toluene | 3.7 | 38.4[a] | 8.5 |
| 1.2 | 100 | 1 | toluene | 5.7 | 17.1[a] | 29.0 |
| 1.3 | 130 | 1 | toluene | 4.8 | 41.3 | 67.0 |
| 1.4 | 130 | 3 | toluene | 4.7 | 61.2 | 79.8 |
| 1.5 | 100 | 1 | ~ | 6.9 | 36.6[a] | 10.6 |
| 1.6 | 100 | 3 | ~ | 6.8 | 65.1[a] | 13.5 |
| 1.7 | 115 | 3 | ~ | 6.9 | 97.7 | 17.3 |
| 1.8 | 115 | 6 | ~ | 6.8 | 99.5 | 24.6 |
| 1.9 | 130 | 6 | ~ | 6.7 | 94.1 | 42.5 |
| 1.10 | 130 | 3 | ~ | 6.7 | 56.5 | 99.8 |
| 1.11 | 130 | 3 | toluene | 9.0 | 91.6 | 72.6 |

[a]During the tests, the setup of the acrylonitrile metering pump was found to be unfavorable owing to too great a dead volume (about 16 ml) (approx. 2 m of line, incorporation of a filter and of valves). After the metered addition, acrylonitrile still present within the line was therefore flushed into the autoclave with toluene, which considerably improved the yield.
[b]Conversion based on acrylonitrile.
[c]Selectivity based on 3-cyclohexenecarbonitrile.

$^1$H NMR (CDCl$_3$, 500 MHz): δ=1.75-2.45 (m, 6 H, 3×CH$_2$), 2.75-2.90 (m, 1 H, CH), 5.55-5.70 (m, 1 H, CH), 5.72-5.80 (m, 1 H, CH). —$^{13}$C NMR (CDCl$_3$, DEPT, 126 MHz): δ=22.9 (−, CH$_2$), 24.6 (+, CH), 25.4 (−, CH$_2$), 28.3 (−, CH$_2$), 122.4 (C$_{quat}$, CN), 123.4 (+, CH), 127.0 (+, CH), –GC: t$_R$=25.9 min (RTX-200 capillary column, 60 m×0.32 mm×1.00 μm, Detector temp.: 300° C., Injector temp.: 250° C., Oven temperature gradient: from 80° C. at heating rate 3° C./min to 250° C.).

Example 2

Preparation of 3- or 4-oxocyclohexanecarbonitrile as a Mixture of cis and trans Isomers A nitrogen-inertized and subsequently evacuated 1.2 l autoclave with an overhead stirrer (2×6 stirrer blades) was charged with 3-cyclohexenecarbonitrile (x) and toluene (y) in a ratio of x:y. 50 bar of $N_2O$ were injected, the mixture was stirred briefly (1400 rpm) and $N_2O$ was, if appropriate, injected repeatedly up to a pressure p. The autoclave was heated to an internal temperature T and stirred at this temperature for a time t. The autoclave was cooled, decompressed to ambient pressure, emptied and rinsed with toluene, and volatile fractions were removed from the combined organic phase under reduced pressure. The residue was distilled under reduced pressure. The isomer mixtures of 3- and 4-oxocyclohexanecarbonitrile (~1:1) were obtained as a colorless liquid in a purity of 98%. The results of the tests are compiled in table 2.

TABLE 2

| Ex. | T [° C.] | p [bar] | t [h] | x:y | C(%)[a] | S (%)[b] | Notes |
|---|---|---|---|---|---|---|---|
| 2.1 | 130 | 50 | 10 | 1:1 | 1.5 | — | — |
| 2.2 | 250 | 50 | 10 | 1:2 | 43.2 | 97.3 | — |
| 2.3 | 250 | 50 | 10 | 1:3 | 54.5 | 92.4 | — |
| 2.4 | 250 | 50 | 10 | 1:5 | 27.8 | 99.0 | — |
| 2.5 | 255 | 50 | 7 | 17:9 | 71.2 | 71.1 | further 46 bar of $N_2O$ injected |
| 2.6 | 260 | 50 | 8 | 2:1 | 84.6 | 6.4 | further 40 bar of $N_2O$ injected |
| 2.7 | 265 | 50 | 8 | 2:1 | 81.6 | 34.1 | further 3 × 40 bar of $N_2O$ injected |
| 2.8 | 270 | 50 | 10 | 10:3 | 80.7 | 8.1 | further 40 bar of $N_2O$ injected |
| 2.9 | 245 | 50 | 13 | 13:3 | 68.0 | 45.1 | further 46 bar of $N_2O$ injected |

[a]Conversion based on 3-cyclohexenecarbonitrile.
[b]Selectivity based on 3- and 4-oxocyclohexanecarbonitrile.

The analysis of the resulting isomer mixture gave: $^1$H NMR (CDCl$_3$, 500 MHz): δ=1.82-1.95 (m, 1 H, CH), 2.00-2.25 (m, 11 H, CH, 5×CH$_2$), 2.27-2.48 (m, 4 H, 2×CH$_2$), 2.51-2.65 (m, 4 H, 2×CH$_2$), 3.05-3.32 (m, 2 H, 2×CH), —$^{13}$C NMR (CDCl$_3$, DEPT, 126 MHz): δ=23.6 (−, CH$_2$), 26.2 (+, CH), 27.5 (−, CH$_2$), 28.5 (+, CH), 29.0 (−, 2 C, CH$_2$), 38.7 (−, 2 C, CH$_2$), 40.6 (−, CH$_2$), 43.0 (−, CH$_2$), 122.4 ($C_{quat}$, CN), 120.8 ($C_{quat}$, CN), 121.1 ($C_{quat}$, CN), 206.0 ($C_{quat}$, C=O), 207.4 ($C_{quat}$, C=O). –GC (RTX-200 capillary column, [60 m×0.32 mm×1.00 μm, Detector temp.: 300° C., Injector temp.: 250° C., Oven temperature gradient: from 80° C. at heating rate 3° C./min to 250° C.): $t_R$ (isomer 1)=43.47 min, $t_R$ (isomer 2)=44.40 min.

Example 3

Preparation of 3- and 4-aminomethylcyclohexylamine as a Mixture of cis and trans Isomers The apparatus used consisted of two 270 ml high-pressure autoclaves with a gas inlet, a line for liquid ammonia and propeller stirrers, which were connected to one another via a line at the bottom of the autoclave such that the contents of the first reactor were transferable to the second reactor by means of elevated gas pressure.

A mixture of 3- and 4-oxocyclohexanecarbonitrile (27.8 g, 228 mmol) was introduced into the first autoclave and the autoclave was closed. After inertization with nitrogen, liquid NH$_3$ (120 g, 7.06 mol) was pumped in. The mixture was then heated to 80° C. with stirring (500 rpm). This achieved a pressure of 50 bar. The second autoclave was initially charged with Raney cobalt 2724 from Grace in an amount which was washed with MeOH (3×20 ml), and the autoclave was closed and inertized. After 2 h, the mixture from the first autoclave was transferred into the second (still at ambient pressure) by opening a valve in the connecting line. 150 bar of H$_2$ were injected into the second autoclave which was heated to 120° C. with stirring. On attainment of this temperature H$_2$ was injected to 200 bar and the pressure was kept constant by injecting further H$_2$. Hydrogenation was effected under these conditions for 3 h until the hydrogen uptake stopped, the autoclave was cooled and the contents were discharged. At the same time, a portion of the catalyst was discharged. Typically, full conversion and a selectivity (GC area %) of 96% were achieved. The experiment was repeated nine times, Raney cobalt (10 g) having been replenished for each new reaction. The collected effluents after NH$_3$ had been evaporated off weighed 270 g. This amount was distilled by means of a distillation apparatus with a Normag column head with a 10 cm, column, filled with wire mesh rings, at bottom temperature of 36-130° C. at 1 mbar. This afforded two fractions (4 and 186 g) and residue (58 g). The main fraction was distilled over at 61° C. and comprised, according to GC, 98.6% of an isomer mixture of 3- and 4-aminomethylcyclohexylamine, and 0.46% of a mixture of 3- and 4- cyanomethylcyclohexylamine (yield 72.4% of theory), amine number 866 mg KOH/g. The results of the experiments are compiled in table 3.

TABLE 3

| Ex. | t [h] | 3-/4-Oxo-cyclohexane-carbonitrile: NH$_3$ | X [g] | 3-/4-Oxo-cyclohexane-carbonitrile: Solv. [g/mL] | Solv. | S (%) | Notes |
|---|---|---|---|---|---|---|---|
| 3.1 | 2 | 30 | 10 | 1:4 | MeOH | 50.1 | — |
| 3.2 | 4 | 60 | 10 | 1:8 | MeOH | 29.1 | — |
| 3.3 | 2 | 30 | 20 | 1:4 | MeOH | 98.2 | — |
| 3.4 | 2 | 30 | 20 | 1:4 | MeOH | 86.4 | — |
| 3.5 | 2 | 30 | 20 | 1:4 | THF | 73.9 | — |
| 3.6 | 2 | 31 | 20 | 2:1 | MeOH | 97.7 | MeOH for introduction of the cat. |
| 3.7 | 2 | 31 | 20 | — | — | 97.6 | Cat. from Ex. 3.6 |
| 3.8 | 2 | 31 | 20 | — | — | 98.3 | Cat. from Ex. 3.7 |
| 3.9 | 2 | 31 | 20 | — | — | 99.2 | Cat. from Ex. 3.8 |
| 3.10 | 22 | 301 | 20 | — | — | 95.9 | Cat. from Ex. 3.10 |

$^1$H NMR (CDCl$_3$, 500 MHz): δ=0.55-1.95 (m, signal cluster, 13 H, 4×NH, 8×CH$_2$, CH), 2.45-2.65 (m, 2 H, 2×CH$_2$N), 2.95 (m, 1 H$_{isomer\ 1}$, CHN), 3.10 (m, 1 H $_{isomer\ 2}$, CHN). —$^{13}$C-NMR (CDCl$_3$, DEPT, 126 MHz); δ=19,8 (−, CH$_2$), 24.7 (−, CH$_2$), 25.0 (−, CH$_2$), 29.5 (−, CH$_2$), 29.8 (−, CH$_2$), 32.4 (−, CH$_2$), 34.6 (−, CH$_2$), 35.5 (+, CH), 36.4 (−, CH$_2$), 37.0 (−, CH$_2$), 38.1 (−, CH$_2$), 39.3 (+, CH), 40.5 (+, CH), 40.6 (−, CH$_2$), 41.2 (+, CH), 45.7 (−, CH$_2$), 46.7 (+, CH), 47.3 (+, CH), 48.4 (−, CH$_2$), 48.6 (−, CH$_2$), 50.4 (+, CH), 50.8 (+, CH). –GC (RTX-5 amine capillary column, 30 m RTX-5 amine, film thickness of 1.5 μm and internal diameter 0.25 mm; temp. program: 5 min isothermal at 60° C., then heating at 15° C./min to 280° C. Detector: FID): $t_R$ (isomer 1)=15.38 min, $t_R$ (isomer 2)=15.42 min, $t_R$ (isomer 3)=15.54 min.

The invention claimed is:

1. A process for preparing at least one cyclic diamine selected from a diamine of the formulae (Ia), (Ib), (Ic) or (Id)

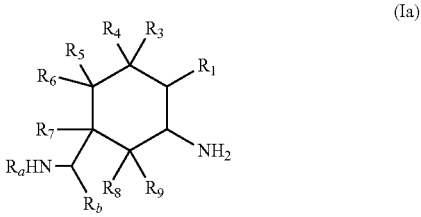

(Ia)

-continued

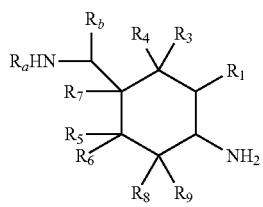
(Ib)

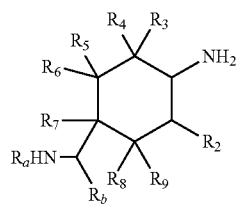
(Ic)

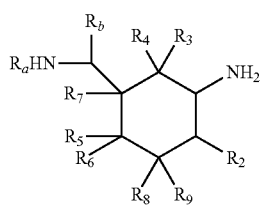
(Id)

wherein the $R_1$, $R_2$, $R_3$, $R_4$, $R_5$, $R_6$, $R_7$, $R_8$, $R_9$, $R_a$, $R_b$ radicals are each independently selected from the group consisting of H and alkyl;

and where $R_1$ or $R_2$ is, or $R_1$ and $R_2$ are each, H, said process comprising at least steps (I) to (II):

(I) reacting at least one compound selected from a compound of the formulae (IIa) and (IIb)

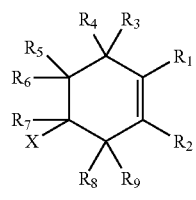
(IIa)

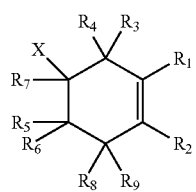
(IIb)

wherein X is a group selected from the group consisting of —CN, —CHO, —CO$_2$R$_c$, —C(=O)R$_b$ and —CH$_2$OH, where R$_b$ is selected from the group consisting of H and alkyl, and where R$_c$ is independently selected from the group consisting of H and alkyl;

with a gas mixture (G) comprising dinitrogen monoxide to obtain at least one compound selected from compounds of the formulae (IIIa), (IIIb), (IIIc) and (IIId)

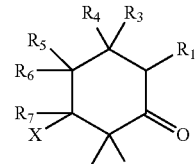
(IIIa)

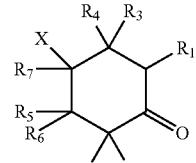
(IIIb)

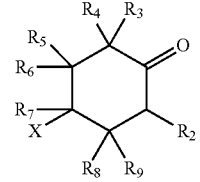
(IIIc)

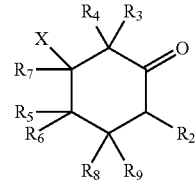
(IIId)

(II) converting the at least one compound obtained in step (I) to at least one compound selected from compounds of the formulae (Ia), (Ib), (Ic) and (Id) by reductive amination.

2. The process according to claim 1, wherein the reaction in step (I) is effected at temperatures in the range from 200 to 265° C.

3. The process according to claim 1, wherein the reaction in step (I) is effected at a pressure in the range from 30 to 55 bar.

4. The process according to claim 1, wherein $R_c$ is independently selected from the group consisting of H and methyl.

5. The process according to claim 1, wherein the gas mixture (G) at least comprising dinitrogen monoxide is the offgas of an industrial process.

6. The process according to claim 1, wherein the conversion step (II) comprises at least steps (a) and (b):
(a) contacting the at least one compound selected from compounds of the formula (IIIa), (IIIb), (IIIc), (IIId), with an amine compound NH$_2$R$_a$, and
(b) hydrogenating the at least one compound obtained in step (a).

7. The process according to claim 6, wherein the amine compound NH$_2$R$_a$ is ammonia.

8. The process according to claim 6, wherein the hydrogenation in step (b) is effected over a catalyst comprising Raney cobalt.

9. The process according to claim 8, wherein the catalyst has been doped with chromium, nickel, iron and/or cobalt.

10. The process according to claim 6, wherein the contacting in step (a) is effected at a temperature in the range from 0 to 150° C.

11. The process according to claim 9, wherein the hydrogenation in step (b) is effected at a temperature in the range from 50 to 150° C. and a pressure in the range from 1 to 300 bar.

12. The process according to claim 10, wherein the hydrogenation in step (b) is effected at a temperature in the range from 50 to 150° C. and a pressure in the range from 1 to 300 bar.

13. The process according to claim 1, in which the at least one compound which is selected from compounds of the formulae (IIa) and (IIb) and is used in step (I) is provided by a process comprising at least step (i):

(i) reacting a compound of the formula (ia)

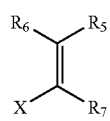

(ia)

with a compound of the formula (ib)

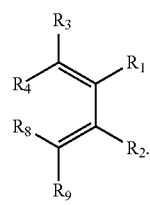

(ib)

14. The process according to claim 13, wherein the reaction in step (i) is effected at a temperature in the range from 20 to 200° C.

15. The process according to claim 13, wherein the reaction in step (i) is effected in a mixture at least comprising the compound of the formula (ia), the compound of the formula (ib) and toluene.

16. The process according to claim 13, wherein the process for providing the compound used in step (I) further comprises at least step (ii)

(ii) distilling the mixture obtained from the reaction in (i).

17. A process for preparing at least one cyclic diamine selected from a diamine of the formulae (Ia), (Ib), (Ic) or (Id)

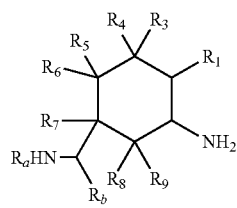

(Ia)

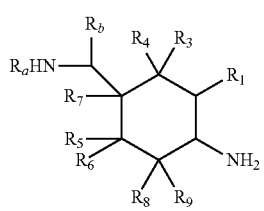

(Ib)

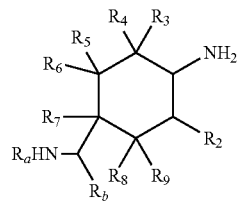

(Ic)

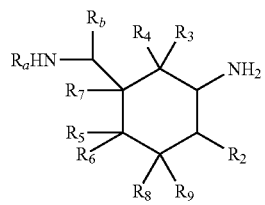

(Id)

wherein the $R_1$, $R_2$, $R_3$, $R_4$, $R_5$, $R_6$, $R_7$, $R_8$, $R_9$, $R_a$, $R_b$ radicals are each independently selected from the group consisting of H and alkyl;

and where $R_1$ or $R_2$ is, or $R_1$ and $R_2$ are each, H, said process comprising at least steps (I) to (II):

(I) reacting at least one compound selected from a compound of the formulae (IIa) and (IIb)

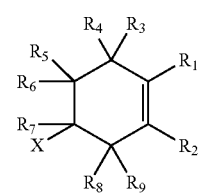

(IIa)

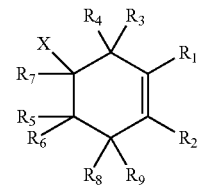

(IIb)

wherein X is a group selected from the group consisting of —CN, —CHO, —CO$_2$R$_c$, —C(=O)R$_b$, —CONR$_c$ and —CH$_2$OH, where R$_b$ is selected from the group consisting of H and alkyl, and where R$_c$ is independently selected from the group consisting of H and alkyl;

with a gas mixture (G) comprising dinitrogen monoxide to obtain at least one compound selected from compounds of the formulae (IIIa), (IIIb), (IIIc) and (IIId)

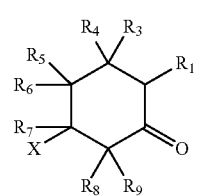

(IIIa)

-continued
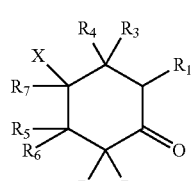
(IIIb)
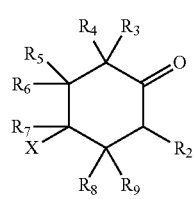
(IIIc)
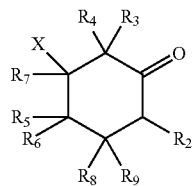
(IIId)
(II) converting the at least one compound obtained in step (I) to at least one compound selected from compounds of the formulae (Ia), (Ib), (Ic) and (Id) by reductive amination.
* * * * *

UNITED STATES PATENT AND TRADEMARK OFFICE
CERTIFICATE OF CORRECTION

PATENT NO.       : 8,592,632 B2  Page 1 of 1
APPLICATION NO. : 13/128508
DATED            : November 26, 2013
INVENTOR(S)      : Dahmen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 241 days.

Signed and Sealed this
Twenty-second Day of September, 2015

Michelle K. Lee
*Director of the United States Patent and Trademark Office*